United States Patent

Holderbaum et al.

[11] Patent Number: 5,917,080
[45] Date of Patent: Jun. 29, 1999

[54] PREPARATION OF 2-CYANO-3,3-DIARYLACRYLIC ESTERS

[75] Inventors: Martin Holderbaum, Ludwigshafen; Karl Beck, Östringen; Alexander Aumüller, Neustadt; Tom Witzel, Ludwigshafen; Guido Voit, Schriesheim, all of Germany

[73] Assignee: BASF Aktiengesellschaft, Ludwigshafen, Germany

[21] Appl. No.: 08/952,667

[22] PCT Filed: May 24, 1996

[86] PCT No.: PCT/EP96/02238

§ 371 Date: Dec. 1, 1997

§ 102(e) Date: Dec. 1, 1997

[87] PCT Pub. No.: WO96/38409

PCT Pub. Date: Dec. 5, 1996

[30] Foreign Application Priority Data

Mar. 31, 1995 [DE] Germany .............. 195 19 894

[51] Int. Cl.$^6$ ................................. C07C 255/00
[52] U.S. Cl. ........................................... 558/402
[58] Field of Search ............................... 558/402

[56] References Cited

U.S. PATENT DOCUMENTS 3,215,724  11/1965  Strobel et al. ................... 260/465

FOREIGN PATENT DOCUMENTS 0 430 023   6/1991   European Pat. Off. .
43 14 035   4/1993   Germany .
44 42 138  11/1994   Germany .

OTHER PUBLICATIONS

Societe Chimiques de France, Paris, Bulletin, vol. 1963, Georges Charles.

*Primary Examiner*—Johann Richter
*Assistant Examiner*—Joseph Murray
*Attorney, Agent, or Firm*—Oblon, Spivak, McClelland, Maier & Neustadt, P.C.

[57] ABSTRACT

A process for preparing 2-cyano-3,3-diarylacrylic esters of the general formula I

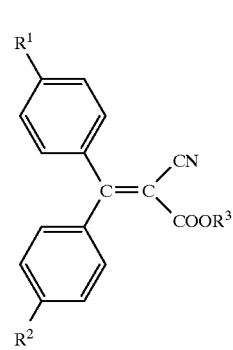

where $R^1$ and $R^2$ are hydrogen, $C_1$–$C_{12}$-alkyl groups, $C_1$–$C_{12}$-alkoxy groups or di($C_1$–$C_4$-alkyl)amino groups and $R^3$ is a $C_4$–$C_{18}$-alkyl group which can be interrupted by ether-functional oxygen atoms, by reacting a benzophenone imine of the general formula II

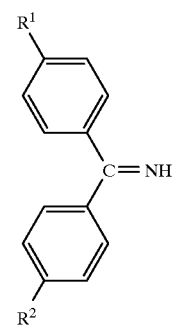

with a cyanoacetic ester of the general formula III

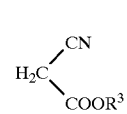

wherein the reaction is carried out at from 20 to 60° C. and, during this, the liberated ammonia is continuously removed from the reaction mixture with the aid of a stream of gas or by reducing the pressure to from 900 to 100 mbar.

8 Claims, No Drawings

PREPARATION OF 2-CYANO-3,3-DIARYLACRYLIC ESTERS

BACKGROUND OF THE INVENTION

1. Field of the Invention

The present invention relates to an improved process for preparing 2-cyano-3,3-diarylacrylic esters of the general formula I

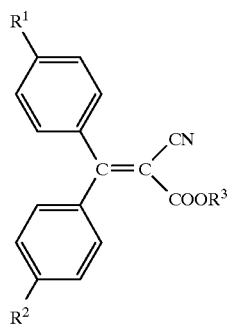

where $R^1$ and $R^2$ are hydrogen, $C_1$–$C_4$-alkyl groups, $C_1$–$C_4$-alkoxy groups or di($C_1$–$C_4$-alkyl)amino groups and $R^3$ is a $C_4$–$C_{18}$-alkyl group which can be interrupted by ether-functional oxygen atoms, by reacting the appropriate benzophenone imines with the appropriate 2-cyanoacetic esters.

2-Cyano-3,3-diarylacrylic esters are highly effective UV absorbers which are used in particular as light stabilizers in plastics and cosmetic products.

2. Description of the Background

It is generally known to prepare compounds of type I from the benzophenones by reaction with cyanoacetic esters (see, for example, EP-A1 430 023, US-A 3 215 724 and DE-A1 43 14 035).

Although this reaction requires the relatively high temperatures of from 70 to 130° C., it takes place only slowly and therefore requires the use of a catalyst, which must subsequently be removed from the product. In addition, unwanted concomitant substances are produced and, for this reason, elaborate purification steps must follow the reaction.

It is furthermore known (Bull. Chem. Soc. Fr. (1963) 1576 (G. Charles)) to prepare ethyl 2-cyano-3,3-diphenylacrylate from benzophenone imine and ethyl 2-cyanoacetate at 70 to 120° C., but this reaction has the disadvantage that colored byproducts are produced at the reaction temperatures, and the liberated ammonia reacts to an interfering extent with the ester moiety of the molecule to give the corresponding amide

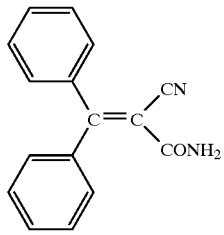

ie. elaborate purification stages are also necessary in this case, especially in order to make the products suitable for use in cosmetic products.

SUMMARY OF THE INVENTION

It is an object of the present invention to make the compounds I available in a simpler and more economic manner than hitherto.

We have found that this object is achieved by an improvement in the process, defined at the outset, for preparing the compounds I, which comprises reacting a benzophenone imine of the general formula II

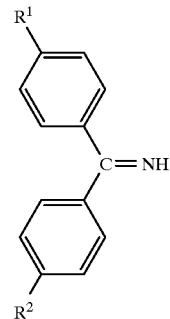

with a cyanoacetic ester of the general formula III

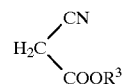

at from 20 to 60° C. and, during this, continuously removing the liberated ammonia from the reaction mixture with the aid of a stream of gas or by reducing the pressure to 900–100 mbar.

DETAILED DESCRIPTION OF THE INVENTION

Compounds I which are particularly important with a view to the use properties are those where $R^1$ and $R^2$ are hydrogen, methyl or ethyl. Further preferred radicals $R^1$ and $R^2$ are methoxy, ethoxy and dimethylamino. The region of light absorption can be shifted somewhat by choice of the substituents $R^1$ and $R^2$ so that the compounds I can be suited to specific light stabilization requirements. The corresponding benzophenone imines II are known or obtainable by known methods (see, for example, Bull. Chem. Soc. cit. and German Patent Application P 44 42 138.9).

Particularly suitable cyanoacetic esters are those with a relatively long-chain alcohol component. Preferred cyanoacetic esters are those derived from 2-ethylhexanol and n-octanol, which are proven components of important light stabilizers. However, other alcohol residues, such as the various isomeric butanols, pentanols, hexanols, heptanols, nonanols, decanols, dodecanols or alcohols derived from long-chain fatty acids can also be constituents of cyanoacetic esters which can advantageously be used. Also suitable as $R^3$ are the various polyoxyethylene radicals such as —$CH_2$—$CH_2$—O—$CH_2$—$CH_3$, —$CH_2$—$CH_2$—O—$CH_2$—$CH_2$—O—$CH_2$—$CH_3$ and their longer-chain homologs, which confer on the compounds I solubility properties which are advantageous in particular for cosmetic formulations.

The process according to the invention is particularly suitable for preparing liquid products I which cannot be separated from the starting materials and byproducts by crystallization. This particularly applies to compounds I where $R^3$ is a longer alkyl or polyoxyethyl [sic] radical.

The reaction of the diaryl ketone imine with the cyanoacetic ester is carried out at from 20 to 60° C., preferably from 25 to 50° C., in particular from 30 to 40° C.

The temperature depends on the thermal stability and on the melting point of the reactants in the reaction mixture. The reaction will tend to be carried out in the higher temperature range for high-melting substances. In order to keep all the reactants in solution, in some circumstances a small amount of solvent will be used.

It is important that the ammonia which is produced during the reaction is removed from the mixture immediately by a stream of gas passed through the solution, or by reducing the pressure to 900–100 mbar, preferably to from 500 to 150 mbar. Preferred gases are inert gases such as nitrogen, but air can also be used.

The reaction has generally proceeded to a conversion of about 85% after about 2–6 hours. An advantageous procedure provides for subsequent workup by distillation, eg. in a thin-film or, in particular, in a falling film evaporator. The distillation preferably takes place in a countercurrent of nitrogen at from 170 to 210° C. under from 1 to 25 mbar. This brief exposure of the reaction mixture to heat increases the conversion by a further 10% approximately, without the quality of the final product suffering in terms of color or the amide content noticeably increasing. Residues of starting materials are stripped off during the distillation and can be reused for a further reaction. The purity of the products prepared in this way is, as a rule, more than 99%, as shown by gas chromatographic analyses.

The process according to the invention can be carried out either batchwise or continuously by methods customary for these purposes.

EXAMPLE

Preparation of (2-ethyl)hexyl 2-cyano-3,3-diphenylacrylate 905 g (5.0 mol) of benzophenone imine were slowly added to 992 g (5.0 mol) of (2-ethyl)hexyl cyanoacetate, and the mixture was stirred at room temperature while passing nitrogen through for 3 h. Subsequently, volatile constituents were removed from the reaction mixture in a thin film evaporator (Sambay, 0.05 m² drying area) with a throughput of 800 g/h at 185° C. under about 8 mbar. The countercurrent of nitrogen during this was about 5 l/h. The bottom product was filtered through active carbon at about 80° C. Product produced in the distillate by subsequent reaction was freed of volatile constituents by subsequent distillation. The overall yield of product was 94%.

The product was obtained as a pale yellow oil with a purity, determined by gas chromatography, of 99.5% and a color number (GARDNER, measured as a 10% by weight solution in toluene) of 2.

We claim:

1. A process for preparing 2-cyano-3,3-diarylacrylic esters of formula I:

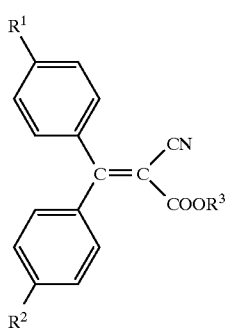

(I)

wherein $R^1$ and $R^2$ are hydrogen, $C_{1-12}$-alkyl groups, $C_{1-12}$-alkoxy groups or di($C_{1-4}$-alkyl)amino groups and $R^3$ is a $C_{4-18}$-alkyl group which optionally is interrupted by ether-functional oxygen atoms, comprising:

reacting a benzophenone imine of formula II

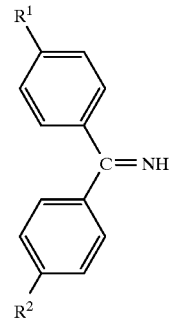

(II)

with a cyanoacetic ester of formula III

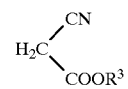

(III)

at a temperature of 20–60° C., thereby continuously liberating ammonia which is continuously removed from the reaction mixture by the flow of a stream of gas or by reducing the pressure over the reaction to 900–100 mbar; and working-up the reaction mixture by distillation in a thin film or falling film evaporator in order to increase conversion to product and to remove residues of starting materials and other volatile compounds from the reaction mixture.

2. The process as claimed in claim 1, wherein the reaction is conducted in the absence of a solvent.

3. The process as claimed in claim 1, wherein $R^1$ and $R^2$ are both hydrogen and the cyanoacetic ester of formula III is 2-ethylhexyl cyanoacetate.

4. The process as claimed in claim 1, wherein the reaction temperature ranges from 25–50° C.

5. The process as claimed in claim 4, wherein the reaction temperature ranges from 30–40° C.

6. The process as claimed in claim 1, wherein the pressure is reduced to 500–150 mbar for the continuous removal of ammonia.

7. The process as claimed in claim 1, wherein the alcohol component of said cyanoacetic ester is an isomeric butanol, pentanol, hexanol, heptanol, nonanol, decanol, or dodecanol.

8. The process as claimed in claim 1, wherein the alcohol component of said cyanoacetic ester is a polyoxyethylene alcohol.

* * * * *

UNITED STATES PATENT AND TRADEMARK OFFICE
CERTIFICATE OF CORRECTION

PATENT NO. : 5,917,080
DATED : June 29, 1999
INVENTOR(S) : Martin HOLDERBAUM, et al.

It is certified that error appears in the above-identified patent and that said Letters Patent is hereby corrected as shown below:

On the title page, item [30] Foreign Application Priority Data should be:

--[30]  Foreign Application Priority Data
   May 31, 1995 [DE] Germany ............ 195 19 894--

Signed and Sealed this

Twenty-fifth Day of April, 2000

Attest:

Q. TODD DICKINSON

*Attesting Officer*   *Director of Patents and Trademarks*